United States Patent [19]

McLaughlin

[11] Patent Number: 5,048,126
[45] Date of Patent: Sep. 17, 1991

[54] PROTECTIVE APPAREL

[76] Inventor: James G. McLaughlin, 4103 Kenwood Dr., Huntsville, Ala. 35810

[21] Appl. No.: 415,658

[22] Filed: Oct. 2, 1989

[51] Int. Cl.$^5$ .................. A41D 13/08; A42B 1/00; A43B 3/16
[52] U.S. Cl. .................................. 2/125; 2/200; 2/243 B; 2/270
[58] Field of Search .................. 2/410, 59, 76, 125, 2/184, 192, 200, 243 B, 243 R, 270, 274, 275, DIG. 6, DIG. 7; 36/9 A, 9 R, 51; 156/161, 166

[56] References Cited

U.S. PATENT DOCUMENTS

| | | | |
|---|---|---|---|
| 1,899,022 | 2/1933 | Duisdieker | 2/243 B X |
| 2,627,126 | 2/1953 | France | 36/9 A |
| 2,707,284 | 5/1955 | Artzt | 2/243 B |
| 3,015,106 | 1/1962 | Van Moer | 2/243 R X |
| 3,187,345 | 6/1965 | Holford | 2/192 X |
| 3,359,658 | 12/1967 | Price | 36/9 R X |
| 3,490,077 | 1/1970 | Brown | 2/243 R |
| 3,657,741 | 4/1972 | Blanco | 2/59 |
| 3,696,445 | 10/1972 | Craig | 2/243 R |
| 3,699,591 | 10/1972 | Breitkopf et al. | 2/243 R |
| 3,719,955 | 3/1973 | Hrubecky | 2/243 R |
| 3,798,503 | 3/1974 | Larsh et al. | 36/9 A X |
| 4,007,835 | 2/1977 | Klothe | 2/274 X |
| 4,407,284 | 10/1983 | Pieniak | 2/270 X |
| 4,480,772 | 11/1984 | Gerndt | 2/243 R X |
| 4,485,495 | 12/1984 | Lunt | 2/200 X |
| 4,493,116 | 1/1985 | Niethammer et al. | 2/243 B X |
| 4,523,336 | 6/1985 | Truman | 2/243 R X |
| 4,532,655 | 8/1985 | Bowditch | 2/125 X |
| 4,642,819 | 2/1987 | Ales et al. | 2/270 X |
| 4,691,390 | 9/1987 | McKeown | 2/243 B X |
| 4,825,564 | 5/1989 | Sorce | 36/9 R X |
| 4,842,666 | 6/1989 | Werenicz | 156/161 |

FOREIGN PATENT DOCUMENTS

| | | | |
|---|---|---|---|
| 663549 | 11/1959 | Canada | 2/243 |
| 1460303 | 12/1965 | France | 2/DIG. 7 |
| 137775 | 1/1920 | United Kingdom | 2/243 R |
| 962355 | 7/1964 | United Kingdom | 2/200 |

Primary Examiner—Thomas B. Will
Assistant Examiner—Scott Cummings
Attorney, Agent, or Firm—John C. Garvin, Jr.; Harold W. Hilton

[57] ABSTRACT

Protective apparel for covering various portions of an individual such as the head, arms, and feet. The protective apparel is made of a heat sealable material which is heat sealed along predetermined surfaces and glued along other surfaces. An elastic material is secured in the material to secure the finished apparel to either the head, arms or feet of the user.

5 Claims, 4 Drawing Sheets

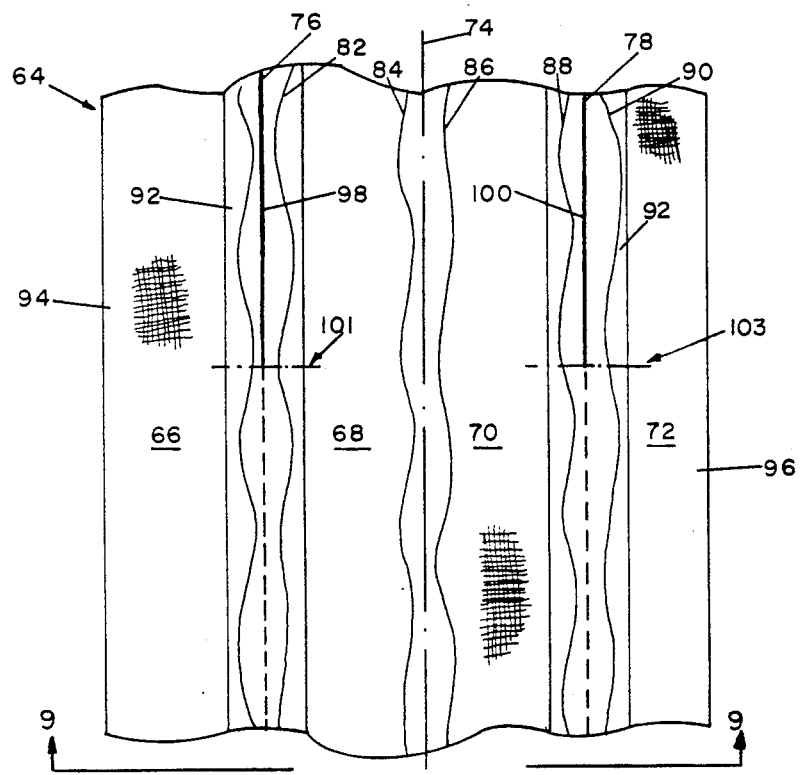
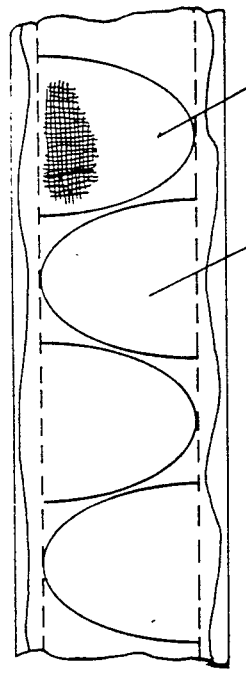
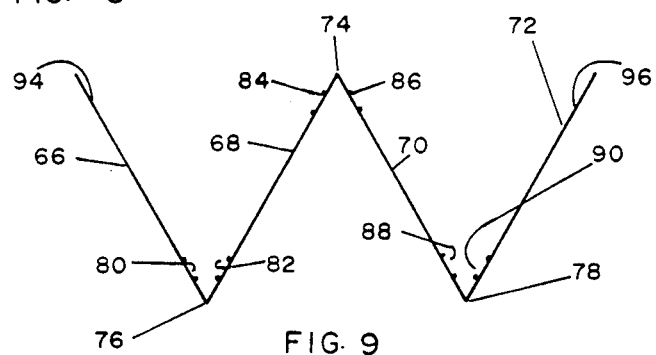
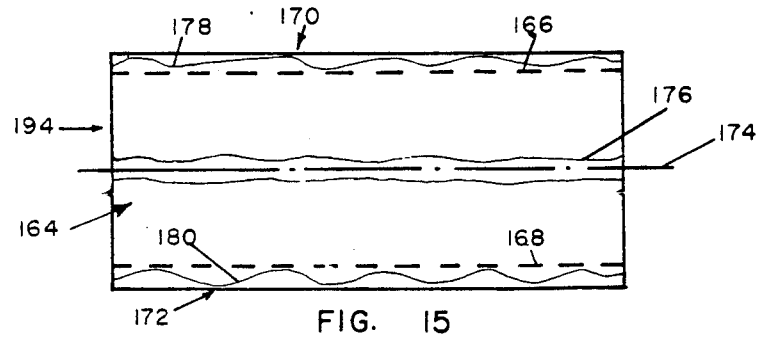
FIG. 8
FIG. 9
FIG. 12
FIG. 15

PROTECTIVE APPAREL

FIELD OF THE INVENTION

The present invention is directed to protective apparel and more particularly to such apparel which covers various portions of an individual such as the head, arms and feet

BACKGROUND OF THE INVENTION

Presently apparel such as coverings for the head (hair), shoe coverings, etc., are made of a single piece of material having an elastic band sewn therein. The covering, typically, is cut from the material in the desired shape (generally circular) or rectangular and the outer edges are folded inwardly to receive an elastic band which is generally hand sewn therein.

An excessive amount of material is generally used in forming such coverings. In forming a cap, for example, a plurality of circles of predetermined diameters are laid out in side-by-side columns on a rectangular sheet and these circles are then cut at the desired diameters. As can be seen the material between the contacting points of the adjacent circles are wasted.

In forming shoe coverings, the edges are generally seamed together by stitching, etc. The seam generally is provided with a "rooster tail" which means that excess material protrudes past the seam. Or, in the absence of such "rooster tails", the material is folded back upon itself and the seam is secured together by ultrasonic techniques. Again, excessive material is required to permit the folding of the material at the seam.

It is an object of the present invention to provide a low cost protective covering to be worn on various parts of an individual.

It is a further object of the present invention to provide such a covering which may be produced in a rapid, facile, and inexpensive process.

BRIEF DESCRIPTION OF THE DRAWING

FIG. 8 is plan view similar to FIG. 5 illustrating the layout pattern for simultaneously producing two shoes according to the principles of the present invention.

FIG. 9 is an elevational view taken along line 9—9 of FIG. 8, showing the sheet of material in partially folded position.

FIG. 12 is an alternate layout view showing another pattern for producing the caps of the present invention.

FIGS. 13-16 are views illustrating alternate layout patterns for producing the shoes of the present invention.

DESCRIPTION OF THE PREFERRED EMBODIMENT

Figure 1:
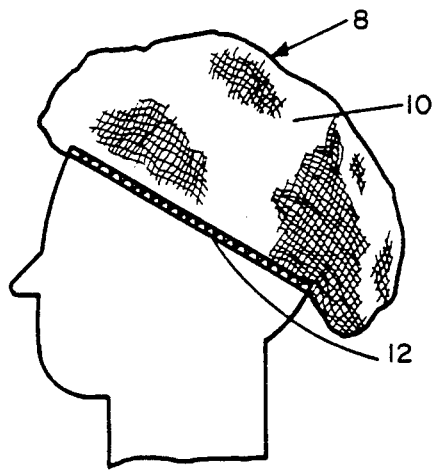
FIG. 1 is a side elevational view of a cap of the present invention shown worn on the head of an individual with the elastic band of the cap expanded around the wearer's head.
Figure 2:
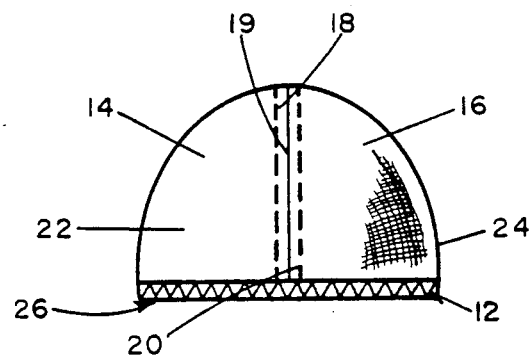
FIG. 2 is a front view of the cap of FIG. 1 and illustrates the elastic band in stretched relation.
Figure 3:
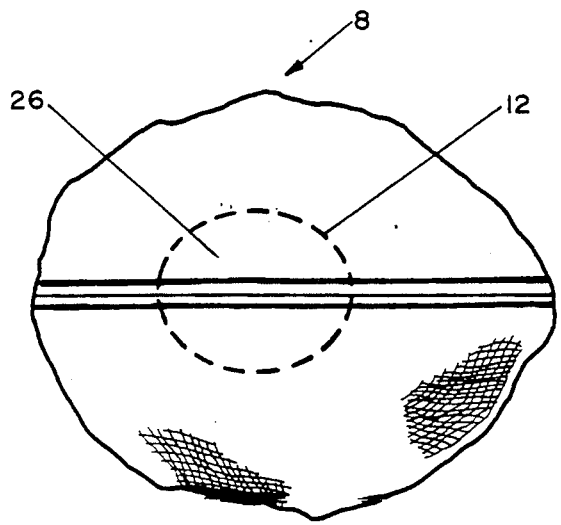
FIG. 3 is a top view of the cap of FIG. 1 with the elastic band in contracted relation.
Figure 4:
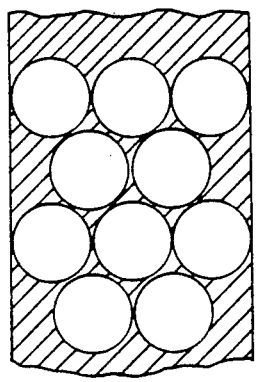
FIG. 4 is layout view of a typical sheet of material showing the pattern of side-by-side circular caps for the cut out procedure as is generally used in the art.

As seen in FIG. 1, a cap 8 is shown to include a body portion 10 having an elastic band 12 for snug fitting relation around the head of an individual. Cap 8 is shown in FIG. 2 as including a pair of sections 14 and 16 having respective edges 18 and 20 disposed in sealed relation along a seal line 19. Sections 14 and 16 define the dome of cap 8. Each section is provided with a lower portion 22 and 24 having the elastic band 12 therein. FIG. 3 is a top view of the cap shown in FIG. 2 and illustrates the elastic band positioned in contracted relation around an opening 26 of the cap. In making the cap of the present invention two sheets of material are provided with the pattern shown in FIG. 5. The sheets are laid one over the other, in overlaying relation and are glued and heat sealed in the manner described hereinbelow.

Figure 5:
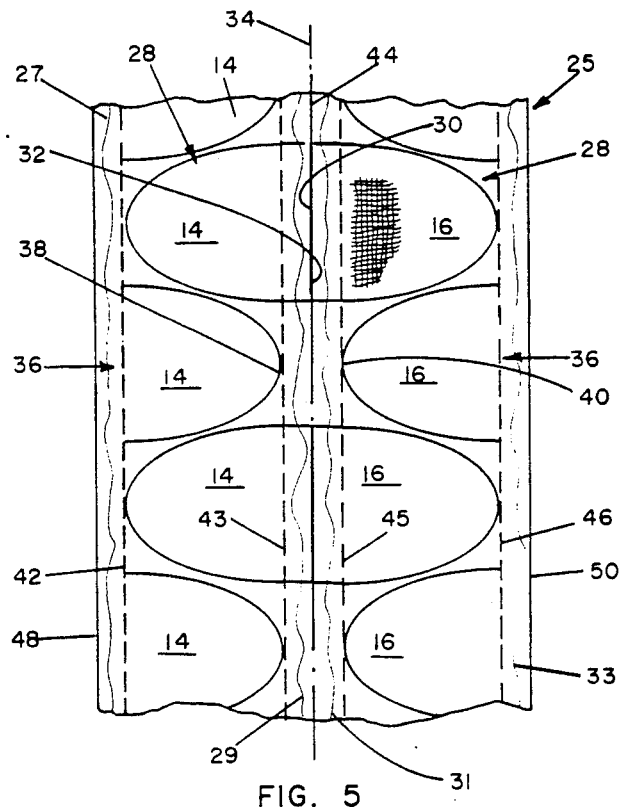
FIG. 5 is a layout view of the pattern used in producing the caps of the present invention.

As can be seen in FIG. 5 a first set 28 of the ellipsoidal half-sections 14 and 16 are positioned in adjacent relation with the straight edges 30 and 32, respectively, of half sections 14 and 16 disposed in spaced relation along a centerline 34. A second set 36 of the ellipsoidal half-sections 14 and 16 is disposed with the apex 38 and 40 thereof, respectively, thereof disposed adjacent to and in spaced relation with centerline 34. Four fold lines 42, 43, 45 and 46 are disposed along the length of the roll of material. Fold lines 42 and 46 are disposed adjacent edges 48 and 50, of material 25. Fold lines 43 and 45 are positioned on opposite sides of centerline 34. A center cut line 44 is disposed along the longitudual centerline 34 of the length of the roll of material 25. A first pair of continuous strips 27 of elastic is positioned between edge 48 and fold line 42. A second pair of strips 29 of elastic is positioned between the centerline 34 and fold line 43 of section 14 along the length of fold line 43. A third pair of strips 31 of elastic is positioned between centerline 34 and fold line 45 of section 20 along the length of fold line 45. A fourth pair of strips 33 of elastic is positioned between edge 50 and fold line 46. Glue is intermittently applied along the length of elastic strips 27, 29, 31 and 33 in a manner described hereinbelow. The sheet of material is then cut along the cutline 44, and each section is folded along fold lines 42 and 43 and 45 and 46 to enclose the elastic band and glue within the folds. The two layers of material, laid out as in FIG. 5, are provided in overlaying relation and the two layers of material are then passed through a heat sealing device where the edges of the ellipsoidal sections 14 and 16 are heat sealed together.

The caps are made in the following sequence. First, two rolls of material are unrolled and placed in overlaying relation and are cut down cut line 44 and the elastic and glue is applied as discussed above. Both sheets are then folded along fold lines 42, 43, 45 and 46 (eight folds) and the folds are pressed together in a presser to secure the elastic in the folds. The folded material is then heat sealed and cut along edges 18 and 20 by a heat sealing device. The cutting and heat sealing is accomplished by a hot cutting bar (not shown) which seals as it cuts the desired configuration.

Figure 6:
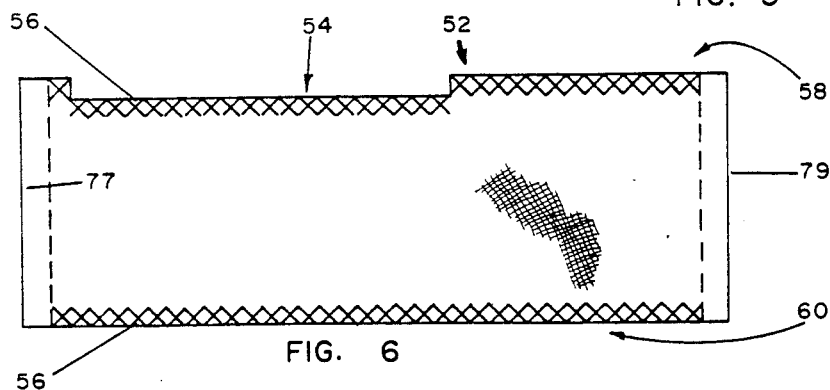
FIG. 6 is an elevational view of a shoe covering of the present invention worn on the foot of an individual.
Figure 7:
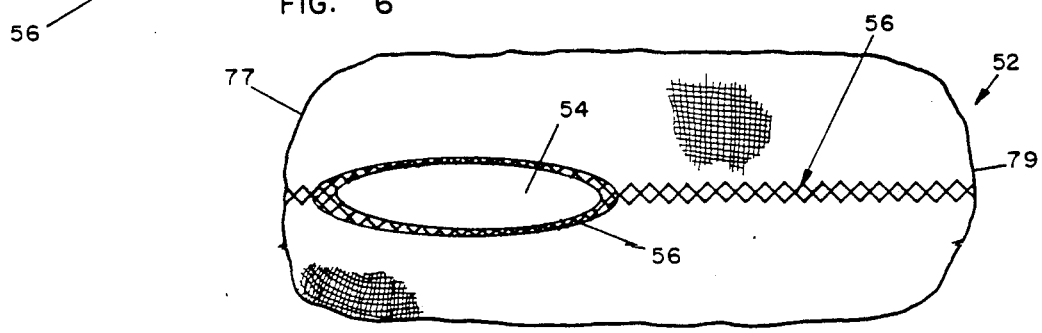
FIG. 7 is a plan view of the foot covering of FIG. 6.

A shoe covering 52 made in accordance with the principles of the present invention is illustrated in FIGS. 6 and 7. Shoe covering 52 is shown to include an opening 54 having an elastic band 56 therearound for snug fitting engagement the ankle of a wearer. The shoe is shown to be provided at its upper and lower peripheral surfaces 58 and 60 with the elastic band 56 is sealed relation thereto.

The shoe covering is simultaneously formed in pairs. FIG. 8 illustrates a roll of material partially unrolled and spread out to form a continuous planar sheet 64 of material. The sheet 64 forms four equal sections 66, 68, 70 and 72 divided by a centerline 74 and two spaced parallel fold lines 76 and 78. To form the shoe covering, a first pair of elastic strips 80 is positioned along the length of one side of fold line 76, a second pair of elastic strips 82 is positioned on the opposite side of fold lines 76 along the length thereof. A third and fourth pair of elastic strips 84 and 86 are similarly placed along fold line (centerline) 74, and, a fifth and sixth pair of elastic strips 88 and 90 are likewise positioned along fold line 78. The elastic strips are held in extended relation along the fold lines. A glue is applied along the length of the fold lines at the same time that the elastic is positioned along the fold lines. At the same time that the glue and elastic is applied, a reinforcing strip 92 is glued partially along the length of fold lines 76 and 78. As shown in FIG. 8, the reinforcing strip is placed over the glue and elastic along the length of fold lines 76 and 78. The reinforcing strip is applied in place at the same time that the glue and elastic is applied.

After the glue, elastic strips and reinforcing material is in place, the sheet of material 64 is folded along fold lines 74, 76 and 78 as indicated in FIG. 9 so that edge 94 engages the elastic strips 84 (and glue) and edge 96 engages the elastic strips 86 (and glue). The folded material is then passed through a sealing device which presses edge 94 along centerline 74, sections 66 and 68 together along fold line 76, sections 70 and 72 together along fold line 78 and edge 96 along centerline 74. Ends 77 and 79, (FIGS. 6 and 7) of each shoe are heat sealed and cut at this stage of the operation. A nonskid surface is provided on the bottom of each shoe.

A pair of slits 98 and 100 are made through the reinforcing strips, partially along the length of the shoe (terminating at lines 101 and 103 as shown in FIG. 8) to form the opening 54 (FIGS. 5 and 6) for receiving the wearer's foot. The material is then cut along the centerline to form a pair of foot coverings.

The shoes are formed in the following sequence. First, a sheet of material is unwound and a small strip (reinforcing material 92) is taken from an edge or edges of the material. A non-skid pattern is then applied to the surface forming the bottom of the shoe. The non-skid surface is printed on the surface with a Gavier Printer. Glue and elastic and the reinforcing strip is then applied to the appropriate locations as discussed above. The material is then folded along the fold lines and ankle opening 54 is produced by the slit through the reinforcing members at the appropriate positions as discussed above and shown in FIG. 8. The sections of material is then pressed along the fold lines (FIG. 9) and cut down cut line 74 and the ends 81 and 83 are cut and heat sealed. Cutting and heat sealing is accomplished by a thin hot wirelike rod which, as it passes through the material at the ends of each shoe it serves to simultaneously cut and seal the shoe ends.

Figure 10:
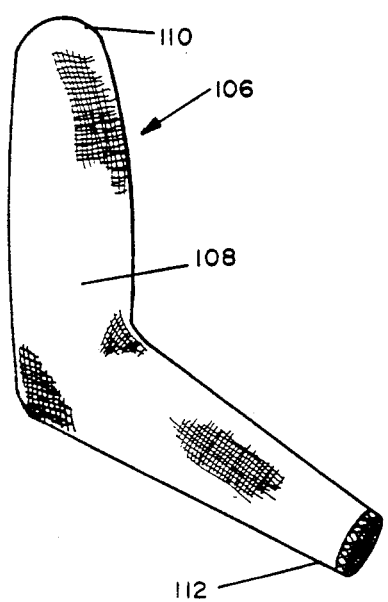
FIG. 10 is an elevational view of a sleeve made in accordance to the principles of the present invention.

FIG. 10 illustrates a sleeve made in accordance to the principles of the present invention. As seen in FIG. 10, a sleeve 106 is shown to include a body portion 108, a shoulder end portion 110, and a wrist end portion 112.

Figure 11:
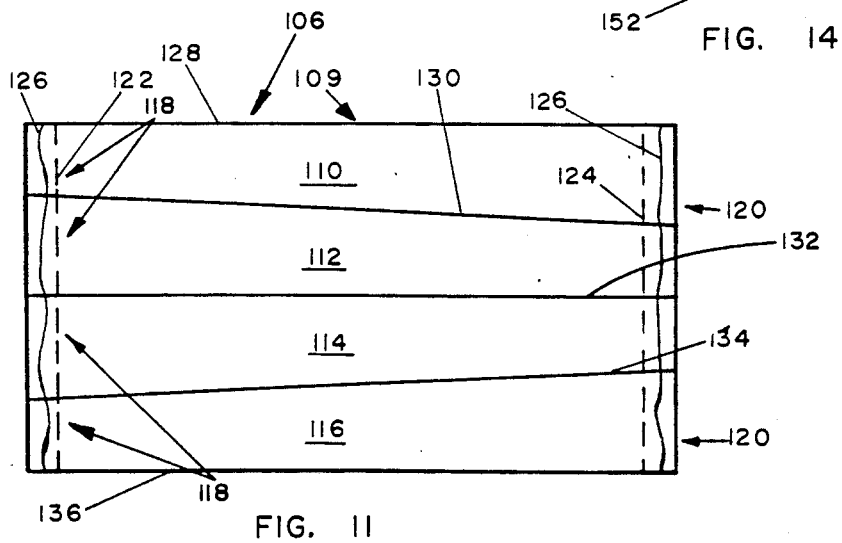
FIG. 11 is a layout of the pattern used in producing the sleeves of FIG. 10.

FIG. 11 illustrates the pattern formed on a roll of material 109 for making the sleeve. Two layers of material having identical pattern layouts are provided for overlaying relation. As seen in FIG. 11 each sleeve is shown to include identical sections 110 and 112, 114 and 116. (Only the lower sheet is shown). Each of the sections 110, 112, 114 and 116 includes ends 118 and 120 and each end 118 and 120 is respectively provided with fold lines 122 and 124. An elastic member 126 and glue is disposed adjacent each end 118 and 120. Ends 118 and 120 are folded to enclose the elastic and glue and the material is heated and pressed along the fold lines. The material is cut and heat sealed along the edges 128, 130, 132, 134 and 136 to form the sleeves.

It is to be understood that while the sleeves are shown to be tapered they may also be made rectangular, if desired.

FIG. 12 illustrates an alternative manner in which the caps of FIGS. 1-3 may be laid out. As seen in FIG. 12 only a single column of caps are laid out with each ellipsoidal half-section 18 and 20 position in a column. Assembly of the sheets of material is accomplished in the same manner as discussed, supra in conjunction with FIG. 5.

Figure 13:
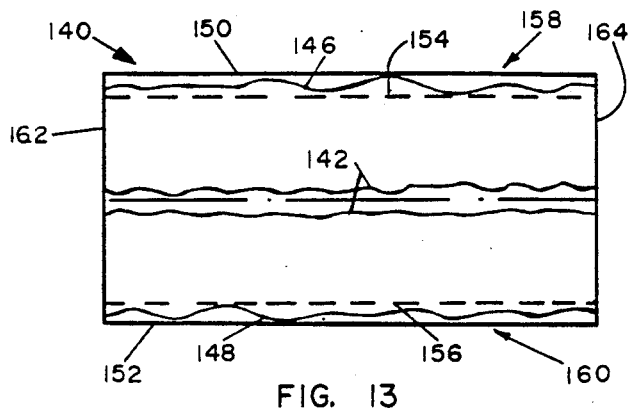
Figure 14:
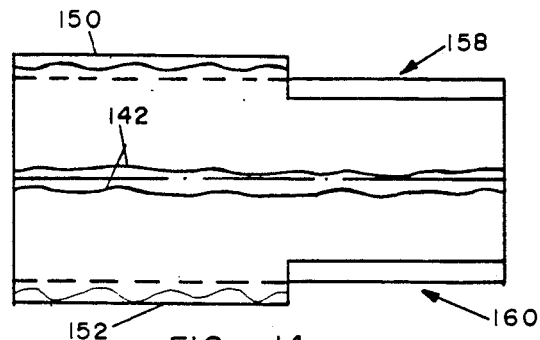

FIGS. 13 and 14 illustrate an alternate approach used in making a shoe covering. As seen in FIG. 13, a sheet of material 140 is laid out and glue and elastic 142 is applied along the centerline 144 thereof. Additional strips 146 and 148 of glue and elastic and glue is applied along the edges 150 and 152 of the sheet. Cuts, indicated by lines 154 and 156 are made perpendicular to edges 150 and 152 and the end areas 158 and 160 are folded over the elastic and glue. The sheet is then folded along centerline 144 for mating relation of the open portions of edges 150 and 152. Sheet 140 is then placed in a presser where the edges 150 and 152 (except at areas 158 and 160) are pressed together to form a glue seam. The folded sheet is then cut and heat sealed by a heat sealer, sealing edges 162 and 164 to form the covering. FIG. 14 illustrates the configuration of sheet 140 while the sheet is still spread out with the edges 150 and 152 folded in the areas 158 and 160.

FIG. 15 illustrates still another alternate approach used in making a shoe covering. As seen in FIG. 15, a sheet of material 164 is provided with fold lines 166 and 168 along the length of edges 170 and 172, respectively. A center fold line 174 is also provided along the centerline of the sheet of material. Glue and elastic 176 is provided along the centerline and glue and elastic 178 and 180 is provided along the edges 170 and 172. The edges are folded along the fold lines 166 and 168 and the sheet of material is folded along the centerline 174.

Figure 16:
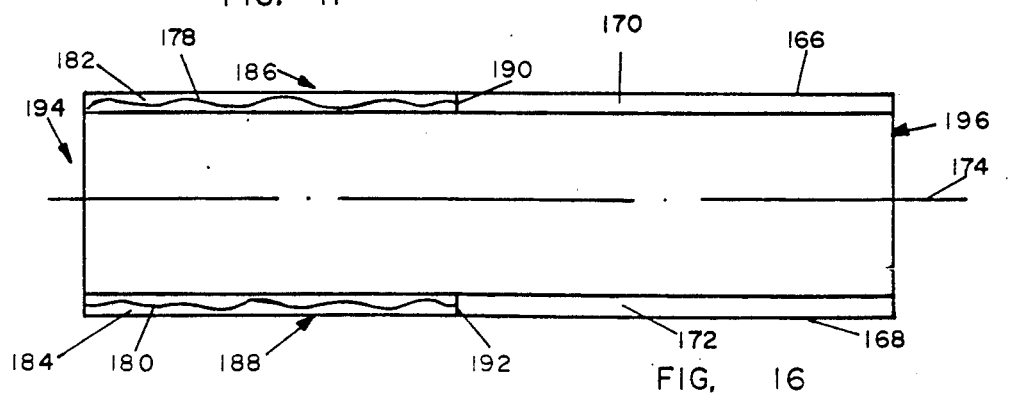

FIG. 16 illustrates the sheet of material 164 of FIG. 15 with the edges 170 and 172 folded along fold lines 166 and 168 as described. With the edges folded as shown in FIG. 16, glue 180 is then applied to the back surfaces 182 and 184 of a portion 186 and 188 of edges 170 and 172. The glue ends at lines 190 and 192. After the elastic and glue has been appropriately applied, the sheet is folded along line 174 and pressed in a presser. The shoe covering is then acted on by a heat sealing device which applies heat for heat sealing ends 194 and 196 thereof and also cuts the material. A reinforcing strip 92 as discussed supra may be used if desired.

It is to be understood that the elastic may be applied in the manner disclosed in U.S. Pat. No. 4,842,666 assigned to H. B. Fuller Company, St. Paul, Minn. Or, if desired, the Nordson Model CF 3200 metering spray head may be used. The spray head is made by the Nordson Corporation, Westlake, Ohio 44145.

It is also to be understood that the coverings may be made of many types of heat sealable materials. Some such materials are: polypropolene, polyethylene, TYVEK, etc., or any of many combined materials, such as polyethylene coated polypropolene.

I claim:

1. A protective shoe covering having a foot receiving opening into which the foot of a person is inserted, said shoe covering disposed for being worn on said foot and comprising:

a pair of similar mating sections of heat sealable material having a rectangular configuration, each said section having a pair of substantially parallel end edge surfaces secured in heat sealed relation, and a pair of substantially parallel upper and lower edge surfaces, said lower edge surfaces being disposed in glued relation along the length thereof and having an elastic band disposed in glued relation along said length, said upper edge surfaces being disposed in glued relation substantially along the length thereof and having said foot receiving opening disposed therein, said foot receiving openings provided with peripheral edge surfaces, said upper edge surfaces of said mating sections having an elastic band disposed in glued relation along the entire length of said upper edge surfaces including said peripheral surfaces, said peripheral surfaces being disposed for folded relation responsive to receiving said elastic band in said glued relation in said folded edges whereby said peripheral edge surfaces of said foot receiving opening are retained in said folded relation solely as a result of said glued relation.

2. A protective sleeve having first and second spaced arm receiving openings into which the arm of an individual is inserted, said sleeve disposed for being worn on said arm comprising:

a pair of similar elongated sections of material having spaced elongated side edge surfaces and spaced end edge surfaces, said side edge surfaces disposed in heat sealed relation along the length thereof, said first of said arm receiving openings defining the shoulder portion of said sleeve and said second of said arm receiving openings defining the wrist portion of said sleeve, said end edge surfaces having an elastic band glued therein around the periphery said openings, the peripheral edge surfaces of said arm receiving openings being disposed for folded relation responsive to receiving said elastic band in said glued relation in said folded edges whereby said peripheral edge surfaces of said arm receiving openings are retained in said folded relation solely as a result of said glued relation.

3. A method of producing a protective head covering to be worn on the head of an individual, said covering included head receiving openings, said method comprising the steps of:

providing a pair of similar sections of heat sealable material with mating edge surfaces having a curved configuration defining the dome portion of said head covering, and lower straight line edge surfaces defining a head receiving opening;

simultaneously applying adhesive and an elastic band around the peripheral surfaces of said head receiving opening;

folding a portion of said material over said adhesive and said elastic band along said peripheral surfaces of said head receiving opening;

pressing said folded portion over said adhesive and elastic for secured relation of said elastic in said folded portion;

heat sealing said mating surfaces of said pair of sections of said dome portion; and cutting said pair of similar sections adjacent said heat sealed mating surfaces, said heat sealing and cutting being simultaneously accomplished.

4. A method of producing a shoe covering to be worn on the foot of an individual, said covering including foot receiving openings, said method comprising the steps of:

providing a pair of similar sections of heat sealable material with a rectangular configuration having a pair of spaced mating end edge surfaces defining the forward and rear ends of said shoe covering, and a pair of upper and lower substantially parallel mating edge surfaces forming the upper and lower surfaces of said covering;

simultaneously applying adhesive and an elastic along said mating surfaces including around the peripheral surfaces of said foot receiving opening;

folding a portion of said material over said adhesive and said elastic band along the peripheral surfaces of said foot receiving opening;

pressing said folded portion over said adhesive and elastic for secured relation of said elastic in said folded portion;

heat sealing mating surfaces of said pair of sections of material for the secured relation thereof to thus form said shoe covering and, cutting said formed covering adjacent said heat sealed mating surfaces, said heat sealing and cutting being simultaneously accomplished.

5. A method of producing a protective sleeve covering to be worn on the arm of an individual, said covering including arm receiving openings, said method comprising the steps of:

providing a pair of similar sections of heat sealable material with a pair of spaced elongated said edge surfaces and a pair of end edge surfaces for forming said arm receiving openings;

simultaneously applying adhesive and an elastic band around the peripheral surfaces of said arm receiving openings;

folding a portion of said material over said adhesive and said elastic band along the peripheral surfaces of said arm receiving openings;

pressing said folded portion over said adhesive and elastic for secured relation of said elastic in said folded portion; and heat sealing said end edges mating surfaces of said pair of sections of material for the secured relation thereof to thus form said covering and, cutting said formed covering adjacent said heat sealed mating surfaces, said heat sealing and cutting being simultaneously accomplished.

* * * * *